United States Patent [19]

Kruger

[11] 4,383,327
[45] May 10, 1983

[54] RADIOGRAPHIC SYSTEMS EMPLOYING MULTI-LINEAR ARRAYS OF ELECTRONIC RADIATION DETECTORS

[75] Inventor: Robert A. Kruger, Salt Lake City, Utah

[73] Assignee: University of Utah, Salt Lake City, Utah

[21] Appl. No.: 211,792

[22] Filed: Dec. 1, 1980

[51] Int. Cl.³ ............................................. G01N 23/00
[52] U.S. Cl. ......................................... 378/19; 378/22; 378/99
[58] Field of Search ..................... 250/445 T, 416 TU; 358/111; 378/19, 99, 22

[56] References Cited

U.S. PATENT DOCUMENTS

| | | | |
|---|---|---|---|
| 4,174,481 | 11/1979 | Liebetruth | 250/416 TU |
| 4,179,100 | 12/1979 | Sashin et al. | 378/19 |
| 4,247,780 | 1/1981 | Webber et al. | 250/416 TU |
| 4,298,800 | 11/1981 | Goldman | 250/445 T |

Primary Examiner—Bruce C. Anderson
Attorney, Agent, or Firm—Thorpe, North & Western

[57] ABSTRACT

A scanning radiographic system employing a multi-linear array. The system includes a source of electronic radiation, which is focused upon the multi-linear array. The multi-linear array includes radiation sensors each of which is adapted to generate an intensity signal as a function of the amount of radiation sensed thereby. Each sensor has associated therewith a means for holding or storing its respective intensity signals. The intensity signals thus held may be continually up-dated to reflect subsequent intensity signals resulting from additional radiation sensed by the respective sensors. An opaque object to be scanned by the radiographic system passes through the beam of radiation in a controlled fashion. This controlled motion is synchronized and coordinated with the shifting of the up-dated intensity signals so that the speed and course of travel of a particular up-dated intensity signal through the holding means of a given group of said sensors is optically aligned with the speed and course of travel of the radiation passing through a given area of the opaque specimen. In this fashion, there is generated one up-dated intensity signal corresponding to a given area of the opaque specimen. These up-dated intensity signals are then collected and processed by a suitable visual system.

22 Claims, 4 Drawing Figures

RADIOGRAPHIC SYSTEMS EMPLOYING MULTI-LINEAR ARRAYS OF ELECTRONIC RADIATION DETECTORS

BACKGROUND OF THE INVENTION

This invention relates to radiographic and other similar systems used to create an image of an opaque specimen by sensing the intensity of a beam of electronic radiation passed therethrough. In particular, the invention relates to scanning slit electronic radiographic system employing multi-linear arrays of electronic radiation detectors.

Broadly speaking, radiography is defined as the technique of producing a photographic image of an opaque specimen by transmitting a beam of electronic radiation through the specimen onto an adjacent photographic film. An image results because the variations in thickness, density, and chemical composition of the specimen block or absorb some of the radiation energy, thereby causing the intensity of the radiation that does strike the photographic film (or other sensor) to be a function of the specimen through which it has passed. Radiography is primarily used in the fields of medicine and industry.

Electronic radiographic systems employ electronic detectors rather than photographic film to sense the amount of electronic radiation that passes through the opaque specimen. Signals generated by the electronic detectors are then processed to form an image which may be displayed on an appropriate electronic device, such as a cathode ray tube. This process of using electronic detectors is broadly referred to as electronic image detection.

Electronic image detection has had a revolutionary impact on radiography in recent years. This is because, in a large part, of the many and varied mathematical and analytical tools available for the processing of the data generated by the electronic radiation detectors. These analytical tools are easily and economically used by means of modern day computers, which makes the handling and processing of large amounts of data a relatively easy task.

In the prior art of radiographic systems, three specific areas have emerged which have had a significant impact on electronic image detection. These areas are: (1) fluoroscopy, (2) computed radiography, and (3) computed tomography. Each of these systems uses different approaches in gathering radiographic image information and combining it to form a desired image.

Fluoroscopy is a term that historically relates to the use of a fluoroscope for X-ray examination. A fluoroscope was a florescent screen, or a screen covered with phosphors, designed for use with an X-ray tube or other suitable source of radiation. Radiation striking the fluoroscope would cause the phosphors to emit light, thereby permitting a direct visual observation of X-ray shadow images of objects interposed between the X-ray tube and the screen. Because fluoroscopy allowed an entire image to be displayed at one time, the term has more recently come to mean a radiographic system displaying an image representing a relatively large area of the opaque specimen. Typically, fluoroscopy involves the use of some sort of image intensifier and video system to allow an entire image to be viewed at one time.

Computed fluoroscopy (hereinafter CF) refers to a combination of an image intensifier and video system plus a high speed digital image processor. The purpose of the processor is to convert the fluoroscopic image to a matrix of appropriate digital signals that can be stored and linearly processed, and eventually displayed.

The most successful use of CF to date has been in the area of time dependent image subtraction. That is, if a low image contrast is present in the fluoroscopic image (such as might exist when iodine is selectively inserted into the opaque specimen so as to provide known attenuation properties of the electronic radiation), CF can be used to enhance the contrast and allow visualization of many internal features of the opaque specimen that were previously not clearly visualized.

Because CF requires the use of a large area image intensifier as well as a video system, the limitations of CF are primarily those of its constituent elements. In particular, the image intensifier limits CF in three ways. First, the field size is presently limited to about 7" diameter (in the opaque specimen) by the currently available 9" image intensifier. As larger image intensifiers are developed (such as a 14" image intensifier being marketed by Phillips Corporation at a cost of over $100,000), larger field sizes will be possible at a significant increase in cost. Besides being very expensive, such systems are bulky, heavy, and therefore require elaborate suspension systems in order reduce their cumbersome maneuverability. Moreover, even these larger image intensifiers are not capable of imaging the typical 14" by 17" field size typically used in chest radiography in the field of medicine.

A second limitation of the image intensifier is the problem of scattered radiation. This is a common problem shared by all prior art large area detectors, and it is particularly noticable for large field sizes and thick specimens. Scattered radiation not only reduces image contrast, but it reduces dose efficiency. That is, the patient (or other opaque specimen) requires an increased exposure of radiation in order to prevent degradation of the image quality. While there are techniques to increase dose efficiency, such as conventional scatter grids, they are not without their cost. For example, conventional scatter grids absorb significant fractions of primary radiation (typically about 40%), thereby reducing the power efficiency of the system. And while other scatter reduction devices have been found which provide little or no attenuation, such as scanning slits or multiple slots, the use of such devices increase the required imaging time.

A third limitation associated with large image intensifiers is the presence of "veiling glare" in the image formation process. Veiling glare results from both electron scatter within the image intensifier as well as light scatter from the input and output phosphors that have been used therein. The presence of veiling glare degrades image quality in much the same way as does the detection of scattered radiation. The amount of glare also increases with field size. For example, in modern day image intensifiers the veiling glare may be anywhere from 10% to 40% depending upon the field size and type of image intensifier employed. It would therefore be an improvement in the art if a large field size, or equivalent, could be obtained without the attendant problems of scattered radiation and veiling glare.

A second prior art technique or method that has evolved in recent years is that of computerized radiography (hereinafter CR). Computerized radiography eliminates the need to use large area detectors by incorporating a fan beam of radiation used in connection with a linear array of detectors. The fan beam of radiation, as its name implies, is a long, but narrow, beam of radiation that falls upon a small linear region of the opaque object at any one time. The width of the fan beam is typically 1 to 3 mm. A large image is formed by passing the opaque object through the fan beam of radiation at a constant velocity with the X-rays (or other radiation) being pulsed once for each fan beam width of travel of the opaque object. Thus, a two-dimensional image is gradually built up one line at a time. This image has the resolution of the width of the fan beam, which as mentioned is typically 1 to 3 mm.

The advantages of CR are many. First, it offers excellent radiation scatter rejection in that the radiation is limited to a very narrow area. Secondly, there is little or no primary attenuation associated with CR because the use of conventional scatter grids is not required. Thirdly, as large an image as is required can be obtained simply by scanning the area over which the image is to be formed until the desired image is built up line by line. Fourthly, veiling glare, or lateral communication of the image information, is minimized because of the limited detector area.

Computerized radiography, or CR, is not without its disadvantages, however. One main disadvantage is the poor image resolution that is achieved, typically being 1 to 3 mm. Secondly, the imaging time is quite long. Typically, the opaque specimen can only travel at a speed of from 2 to 6 centimeters per second because each image element must be exposed for a minimum time. Typically, a large number of photons must be detected for each image element in order to have a useful image. However, the number of photons, or photon flux, that is available from the radiation source (such as X-ray tubes) is limited by heat loading constraints. Thus, the number of photons striking the imaging element must be controlled by the speed of the opaque specimen. The total imaging time then becomes the product of the number of image lines (which is usually around 250 for a typical radiography image) and the exposure time per line. In contrast, the imaging time for computerized fluoroscopy is much shorter because all 250 lines (or whatever number of lines are employed) are formed simultaneously.

Some prior art techniques have been used in order to decrease the imaging time associated with CR. For example, it is possible to design the source of radiation so that it may operate at a higher voltage thereby increasing the flux density as well as the tissue penetration. However, the disadvantage of such higher voltages is a loss of contrast for certain types of popular imaging substances that are selectively inserted into the patient or other opaque specimen. This is particularly true with iodine which is a commonly used substance injected into patients so as to highlight certain systems within their bodies.

It would therefore be desirable to develop a system that provided the advantages of computerized radiography while at the same time improving the image resolution and the imaging time. A radiographic system achieving this desired goal is described herein.

SUMMARY OF THE INVENTION

A general object of the present invention is to provide a radiographic system that allows a large area image to be generated with good resolution in a relatively quick imaging time.

A particular object of the present invention is to improve the present single linear array detection capability in two ways: (1) to improve the resolution, and (2) to increase the imaging speed.

A further object of the present invention is to provide a radiographic system that employs scatter reduction devices having desirable scatter rejection properties without undesirable attenuation and loss of resolution.

Another object of the present invention is to provide a radiographic system capable of generating a large area image in a short time without using needlessly high voltages, nor requiring the use of heavy, cumbersome, bulky equipment.

An additional object of the present invention is to provide a radiographic system that eliminates veiling glare.

Still a further object of the present invention is to provide such a radiographic system that employs a multilinear electronic radiation array that is lightweight, relatively inexpensive, easy to operate, and reliable in its performance.

Still an additional object of the present invention is to provide such a radiographic system that offers improved dose efficiency and power efficiency.

The above and other objects of the present invention are realized in an illustrative embodiment that includes a beam of electronic radiation generated by a suitable source of electronic radiation. The beam of electronic radiation is directed towards, and aligned with, an array of electronic radiation detectors. Each of the detectors on the array is adapted to generate a signal having a magnitude proportional to the amount of radiation it senses. The array also includes, as an integral part thereof, signal processing capabilities whereby the signals generated by each of the detectors may be stored in respective storage elements. These stored signals, at controlled time intervals, are all shifted to the storage elements of other, adjacent, detectors. Once the signals have been shifted, the signals are augmented by new signals, if any, generated by the respective detectors of the storage elements in which the signals are stored. After having been shifted through several storage elements, these augmented signals may exit from the array to be further processed and conditioned so as to enable an image to be created through a suitable visual system.

In connection with the above shifting and processing of radiation signals, the opaque specimen is passed between the source of electronic radiation and the array at a controlled speed and in a known pattern. This controlled speed is synchronized with the controlled time intervals at which the signals are shifted from storage element to storage element. Furthermore, the shifting pattern—that is the sequence that the signals follow as they are shifted from storage element to storage element within the array—is designed to be the same as the movement pattern of the opaque specimen through the beam of electronic radiation. When the shifting pattern of the detector signals is the same as the movement pattern of the opaque specimen, a non-blurred image may be generated. That is, each pixel, or small area, of the image is generated from radiation that passes through a corresponding small area of the specimen. At any instant of time, this radiation falls upon a given detector and generates a signal for that pixel. As the specimen moves, causing the radiation passing through the same small area thereof to likewise move and fall upon an adjacent detector, the pixel signal generated prior to the movement is shifted to the storage element associated with the detector receiving the radiation after the movement. At each storage element, the resolution of the pixel signal is augmented by having it updated to reflect the amount of radiation passing through the corresponding area of the specimen at that particular time. In this fashion, each pixel in the accumulated image results from an integration process. This process is commonly referred to as a time delay and integration (TDI) mode.

In one embodiment of the invention, the two dimensional array is a charge coupled device (CCD) which is operated in the TDI mode. The charge coupled device includes columns of image sensing elements that are tied to a vertical analog transport register. At the top of each vertical analog transport register is a horizontal analog transport register. The image sensing elements generate packets of electrical charge as a function of the radiation sensed thereby. These charge packets are passed along the column shift registers. After the charge packet which resulted from the charge accumulated at a first image sensor in a column of the CCD array has passed to a second element in the same column, the charge which accumulates at the second sensor is added to that already in the register. In this way, charge is accumulated at each successive point along the register until it passes into the horizontal shift register. When the opaque specimen is scanned along the CCD matrix in the same direction as the columns and at the same rate as the charge is passed from line to line (each line representing a row of image sensing elements), a non-blurred image results with each pixel in the accumulated image being the result of N T seconds of integration, where N is the number of lines in the detector, and T equals 1/F, F being the clocking frequency of the vertical shift registers. The horizontal analog transport register is loaded in parallel with charge packets from each vertical analog transport register, in response to the vertical clock signal. These charge packets may be serially clocked out of the horizontal analog transport register at a sufficiently fast rate so as to completely empty it prior to having it reloaded in parallel fashion at the next clocking frequency of the vertical shift register. The charge packets exiting the horizontal register may then be sent to an appropriate data processor where they can be digitized and processed so as to create and display a visual image.

BRIEF DESCRIPTION OF THE DRAWINGS

The above and other objects, features, and advantages of the invention will be more apparent from the following more particular description presented in connection with the accompanying drawings, in which.

DESCRIPTION OF THE PREFERRED EMBODIMENTS

The invention herein disclosed is best understood by reference to the figures wherein like parts are designated with like numerals throughout.

Figure 1:
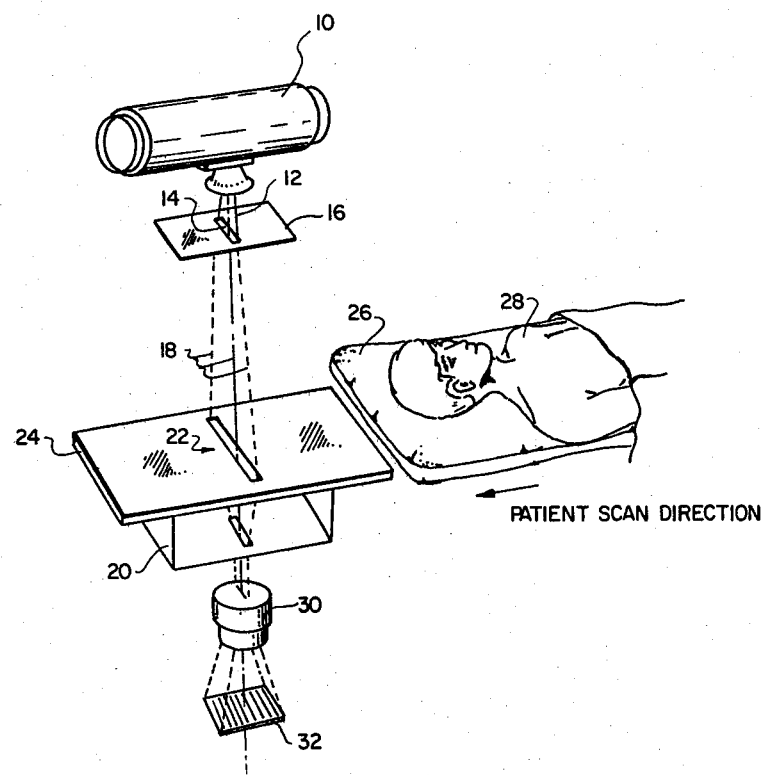
FIG. 1 is a perspective representation of a scanning radiography system employing a multi-linear array.

Referring first to FIG. 1, there is shown a perspective representation of a scanning radiography system of the type herein disclosed as it could be employed for a medical application. A source of electronic radiation 10, such as an X-ray tube, generates a beam of electronic radiation 12. This electronic radiation, or ER, passes through a slit 14 of a collimator 16. The purpose of the collimator 16 is to form the ER beam 12 into a fan beam, represented symbolically in FIG. 1 by the dotted lines 18. The fan beam 18 is directed towards an image intensifier 20. At the point where the fan beam 18 strikes the upper surface of the image intensifier 20, shown generally at 22 in FIG. 1, it covers an area of from 1 to 2 cm. wide by about 20 to 25 cm. long. The upper surface of the image intensifier 20, designated as 24, is suitably adapted to interface with a specimen table 26 upon which a patient or other opaque object 28 may be placed. The specimen table 26 is then caused to move over the upper surface of the image intensifier 24, thereby allowing the fan beam 18 to selectively penetrate those portions of the patient 28 that are to be examined.

As the ER fan beam 18 passes through a patient 28, or other opaque object, various amounts of the radiation will be absorbed depending upon the thickness, density, and chemical composition of the specimen. In particular, for medical applications, it is quite common to inject a substance having known absorption properties, such as iodine, into the patient 28 so that those portions of the patient (e.g., the circulatory system) having the iodine therein will be visible on the ultimate radiography image that is produced. For purposes of this application, it is sufficient to note that the ER fan beam 18 exiting from the patient 28 will have a non-uniform intensity due to the physical and chemical makeup of the patient through which it has passed. This non-uniform radiation is intensified by the image intensifier 20 and directed to a lens 30, or other suitable optically focusing device, which directs and focuses the radiation upon the surface of a multi-linear array 32.

Figure 2:
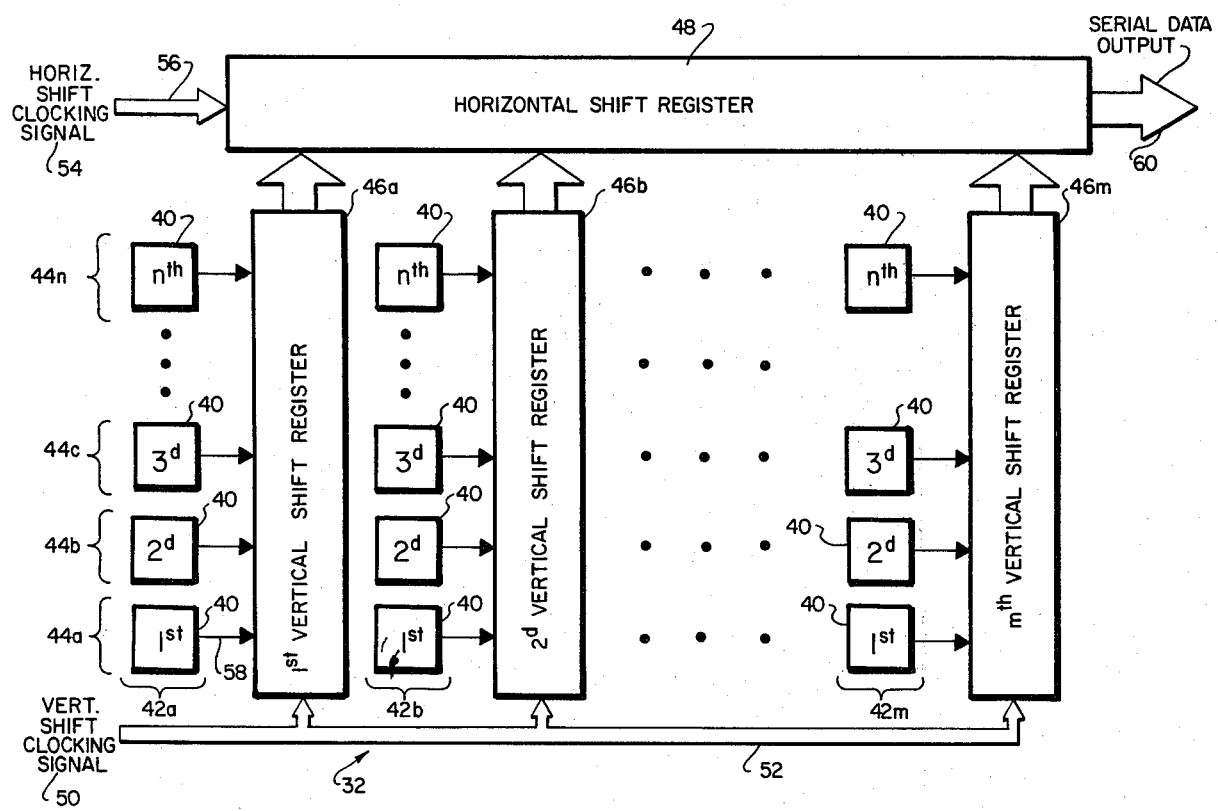
FIG. 2 is a block diagram of an m×n multi-linear array.

In order to fully appreciate and understand the invention herein disclosed, it will be helpful to understand the operation of the multi-linear array 32. Accordingly, a block diagram of the preferred embodiment of a multi-linear array 32 is shown in FIG. 2. The array 32 comprises a plurality of image sensing elements 40 arranged in a particular pattern. In FIG. 2, for example, these image sensing elements 40 are arranged in a plurality of columns, 42a, 42b, . . . 42m where m is a finite integer. The first image sensing elements 40 of the columns 42a, 42b, . . . 42m are mutually aligned so as to form a row of image sensing elements 44a. Subsequent rows of image sensing elements 44b, 44c, . . . 44n are similarly formed by the second, third, . . . and nth image sensing elements 40 of each column, where n is also a finite integer. Thus configured, it is seen that the image sensing elements 40 comprise an m by n array of image sensing elements.

In the preferred embodiment, as shown in FIG. 2, each of the image sensing elements 40 arranged in the first column of sensors 42a are tied to a first vertical shift register 46a. Similarly, the image sensing elements of the column 42b are coupled to a second vertical shift register 46b. The shift registers of each succeeding column, up through 42m, are likewise connected to respective vertical shift registers. A horizontal shift register 48 is coupled to each of the vertical shift registers 46a, 46b, ... 46m, so as to allow the contents of the vertical shift registers to be loaded in parallel into the horizontal shift register 48.

The vertical shift registers 46a, 46b, ... 46m are controlled via a vertical shift clocking signal 50 directed to each register over signal bus 52. Similarly, a horizontal shift clocking signal 54 is directed to the horizontal shift register 48 over a separate signal bus 56. As depicted in FIG. 2, the vertical shift registers 46a, 46b, ... 46m, as well as the horizontal shift register 48, are parallel-in, serial-out registers. Each of the vertical shift registers receives parallel input data from the image sensing elements 40 connected thereto. The horizontal shift register 48, on the other hand, receives parallel input date from each of the vertical shift registers.

Each of the image sensing elements 40 is adapted to generage a signal as a function of the intensity of the radiation falling thereupon. Thus, for example, the first image sensing element of column 42a generates a signal that is directed to the vertical shift register 46a over the signal line 58. This signal is stored in a respective storage element of the vertical shift register 46a. Similar storage elements are present in the vertical shift register 46a for each of the image sensing elements 40 connected thereto. For convenience, these storage elements will be referred to as the first, second, third, ... nth storage elements of their respective shift registers. When the appropriate vertical shift clocking signal is present, the signal stored in the first storage element of a given vertical shift register is shifted to the second storage element of the same register. Simultaneously, the signal stored in the second storage element is shifted to that of the third storage element, and so on, with the signal stored in the nth storage element being shifted out of the vertical shift register into the horizontal shift register 48. As a given signal is thus shifted up through one of the vertical shift registers 46a, 46b, ..., or 46m, it passes through the storage elements corresponding to each of the image sensing elements 40 of the respective column 42a, 42b, ..., or 42m attached to that particular shift register. While the signal is present in each of these storage elements, it may be augmented by additional signals received from the respective image sensing element 40. This augmentation is explained more fully below.

To illustrate the above process, consider a signal $X_1$ that is generated by the first image sensing element 40 of the first column 42a. This signal is stored in the first storage element of the vertical shift register 46a. In response to the vertical shift clocking signals 50, this signal $X_1$ will be shifted to the second storage element of the shift register 46a. While there, it will be augmented with an additional signal, $X_2$, generated by the second image sensing element 40 of the column 42a. Thus, the signal present in the second storage element of the shift register 46a is now $X_1+X_2$. In response to the next vertical shift clocking signal 50, this signal, $X_1+X_2$, will be shifted to the third storage element of the shift register 46a. While there, it will be augmented with a signal $X_3$ generated by the third image sensing element 40 of the column 42a. In a like manner, the signal is augmented at each of the storage elements of the shift register 46a as it is shifted therealong. Thus, the signal that ultimately is shifted out of the shift register 46a into the horizontal shift register 48 is a signal, $X_T$ that may be expressed as:

$$X_T = \sum_{i=1}^{n} X_i$$

where $X_i$ represents the signal generated by the ith image sensing element 40 at the ith time interval as defined by the vertical shift clocking signal 50.

In order to empty the horizontal shift register 48 of all the signals that have been loaded in parallel therein with response to the vertical shift clocking signal 50, it is necessary that the horizontal shift clock signal 54 operate at a frequency that is at least m times as fast as the frequency of the vertical clocking signal 50. This is because the horizontal shift register 48 will typically be comprised of a series of storage elements similar to the vertical shift registers 46a, 46b, ... 46m; and in order for a signal to be shifted from the extreme left of the horizontal shift register 48 (as depicted in FIG. 2) through all of these storage elements and out the serial data output bus 60 at the opposite end thereof, it is necessary that at least m horizontal clocking signals occur in order to completely empty the horizontal shift register 48 of all the signals stored therein.

A preferred method of constructing the multi-linear array 32 shown in FIG. 2, although not the only method that could be used, is through the use of a two dimensional charge coupled device (CCD). A CCD device offers the advantage of allowing the vertical shift registers 46a, 46b, ... 46m, at well as a horizontal shift register 48, to be easily fabricated on the same substrate as the image sensing elements 40. The operation of a two-phase CCD shift register, while not novel to this invention, is depicted in FIG. 3 and is presented herein as being exemplary of how the multi-linear array 32 may be constructed and operated.

Figure 3:
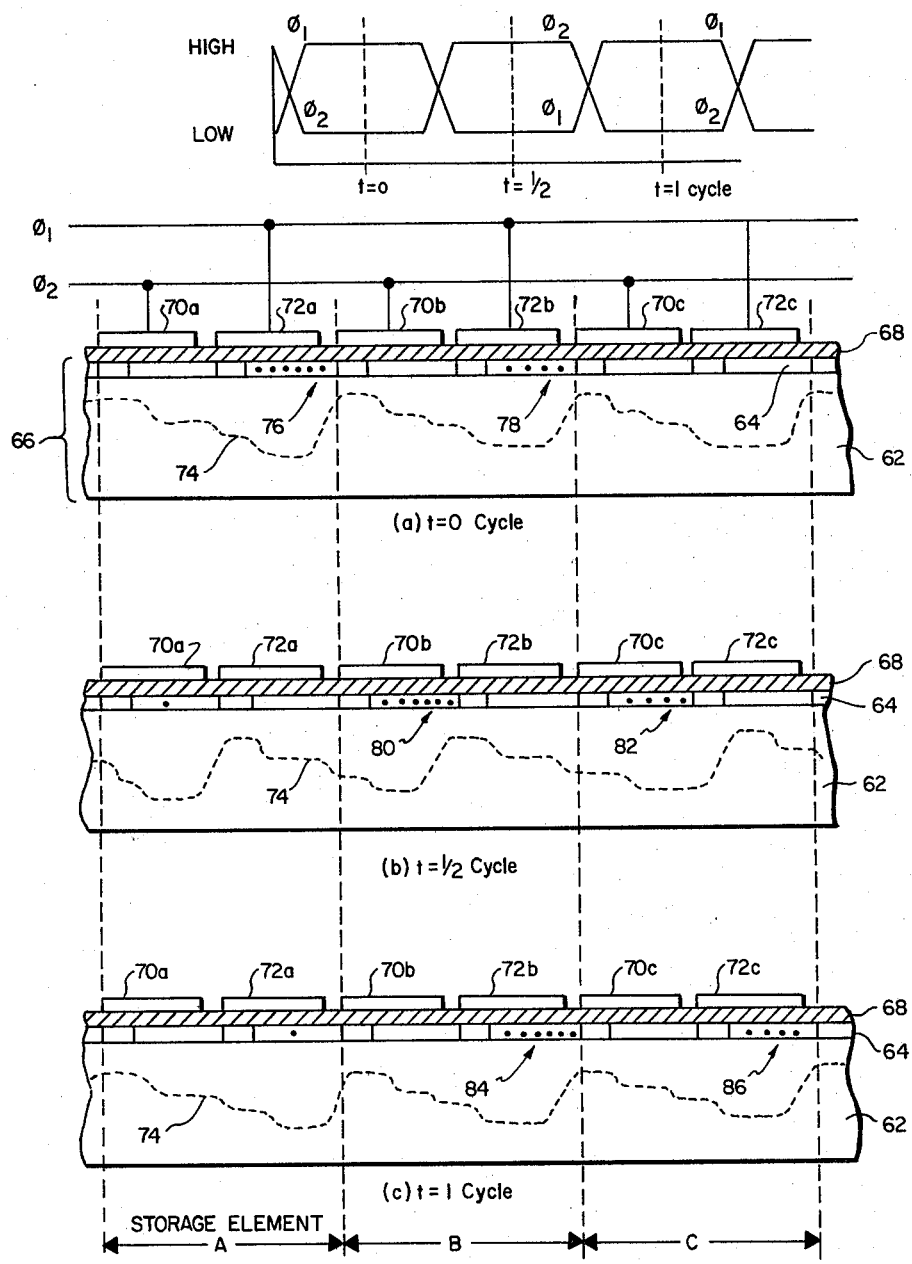
FIG. 3 is a timed schematic representation of a two-phase charge coupled device shift register, including clock signals, showing how finite bundles of charge are shifted from one storage element to another.

In FIG. 3, two complimentary clock voltage waveforms $\phi_1$ and $\phi_2$ are respectively connected to alternate closely-spaced gate electrodes on the surface of a thin insulating layer 68 on a piece of silicone 66. An upper layer 64 of the silicone is n-doped. The substrate 62 of the silicone is p-doped. The $\phi_1$ clock signal is connected to alternately spaced gate electrodes 70a, 70b, 70c, ... Similarly, the clock voltage $\phi_2$ is connected to the alternately spaced gate electrode 72a, 72b, 72c, ... The dotted line 74 is symbolic of the potential wells created by the clock voltage waveforms $\phi_1$ and $\phi_2$. That is, a deep potential well which attracts electrons is created under an electrode where the clock voltage is high and disappears under an electrode where the clock voltage is low. Thus, in FIG. 3(a), which represents in reference to the waveforms depicted at the top of the figure the condition at time $t=0$, the potential well under gate electrodes 70a, 70b, and 70c is low (or shallow) because the clock voltage wave form $\phi_2$ connected to each of these gate electrodes is low at that particular time. In a similar fashion, the potential well under electrode 72a, 72b, and 72c is deep (or large) at this time because the clock voltage waveform $\phi_1$ connected thereto is high. For illustrative purposes, it is assumed that at time $t=0$ that a finite charge packet of 7 electrons (represented symbolically in FIG. 3 as seven dots shown generally at 76) is in the potential well under gate electrode 72a in the storage element "A". Similarly, a finite charge packet of four electrons, shown generally at 74 is in the potential well under gate electrode 72b is in storage element "B". At t=½ cycle later, FIG. 3(b), the potential well under gate 72a has collapsed due to $\phi_1$ having gone low and, since at the same time the adjacent electrode 70b connected to $\phi_2$ has gone high, the seven electron charge packet has been attracted to the new potential well under electrode 70b, as shown generally at 80. Similarly, the charge packet of four electrons has been attracted to the new potential well under electrode 70c, as shown at 82. Another half cycle later, at t=1 cycle, the potential well under electrode 70b has collapsed with $\phi_2$ going low as shown in FIG. 3(c). Thus, the electron packet of seven electrons moves to the new well under electrode 72b as shown at 84. In a like fashion, the charge packet of four electrons has moved to the new potential well now existing under gate electrode 72c, as depicted at 86.

In the fashion above described, a finite charge of electrons (or other charged bundles, such as "holes") may be shifted along the two-phase CCD shift register as controlled by the clock signals $\phi_1$ and $\phi_2$. This type of shift register is especially well suited for the application herein disclosed in that the image sensing elements 40 typically generate a finite bundle of charge (either holes or electrons) as a function of the radiation intensity falling thereon. Moreover, as this finite charge is shifted through the register, at the various storage element sites (labeled "A", "B", & "C" in FIG. 3), it may be readily augmented by merely adding electrons (or holes) to those already present. Thus, by connecting a conductive path between the image sensing element 40 and each respective storage element site, the signals (finite charge packets of electrons or holes) generated by each image sensing element 40 are easily added to the prior existing signal.

CCD two-dimensional image arrays of the type that could be employed by this invention are commercially available. For example, Fairchild Semiconductor, Inc. manufactures a 380×488 image array that is ideally suited for this invention. The model number for such an image array is #CD221CDC. The operation of such an array is fully detailed and understood by those skilled in electronic art through the specification sheets that accompany such devices.

Figure 4:
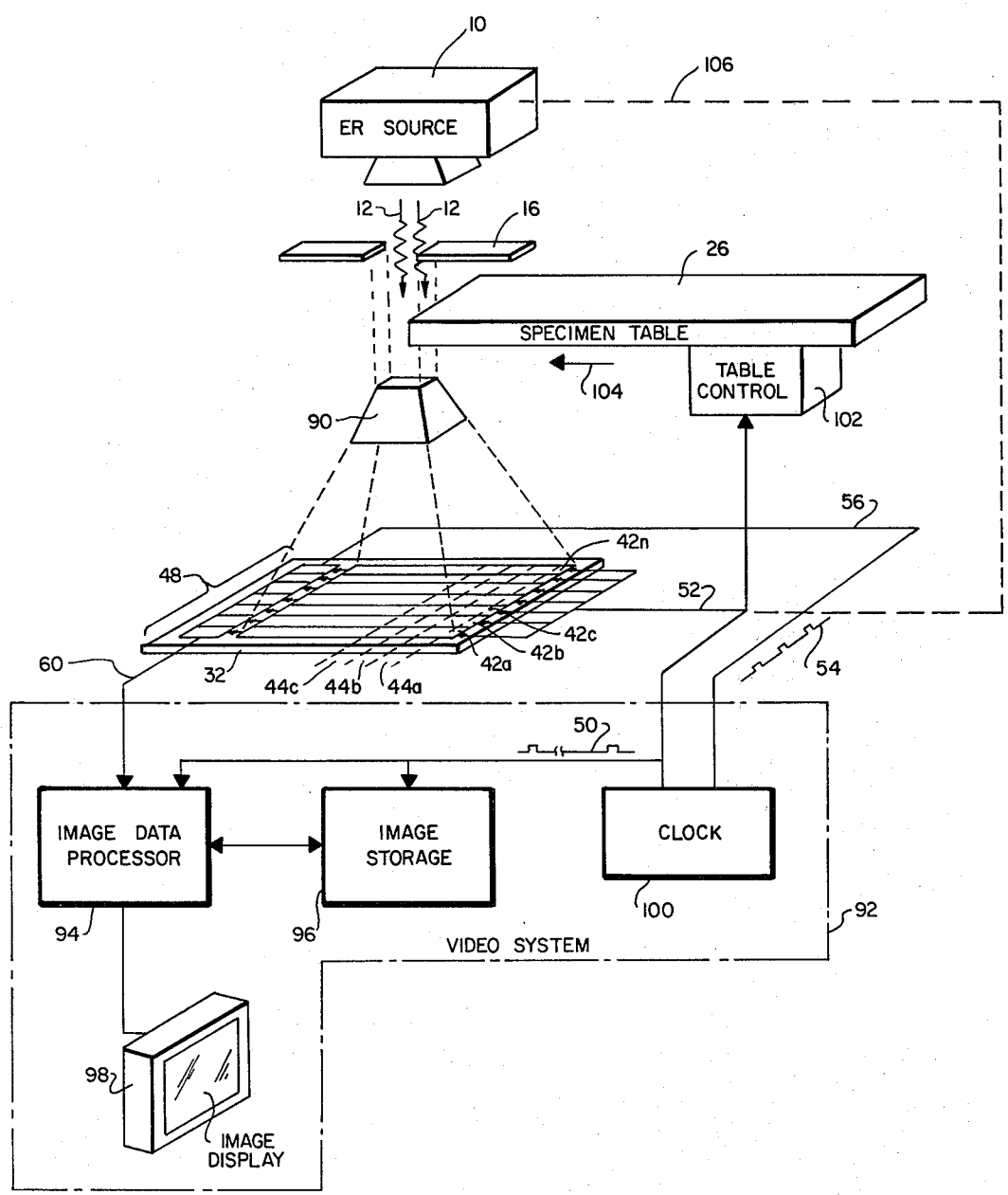
FIG. 4 is a block diagram of a scanning radiography system employing a multi-linear array, including a suitable visual system and a controlled-motion specimen table.

Referring now to FIG. 4, there is shown a block diagram of a scanning radiography system of the type disclosed herein. Portions of the block diagram of FIG. 4 are depicted in perspective so as to facilitate the explanation and description of the system which follows.

As discussed in connection with FIG. 1, a source of electronic radiation (ER) 10 generates a beam of ER radiation 12. This beam of radiation 12 passes through a collimator 16. The purpose of the collimator 16 is to limit the beam to a known area. This beam of radiation 12 is symbolically represented in FIG. 4 as the wavy arrows.

The beam of ER radiation 12 is directed towards and falls upon an intensifier/lens unit 90. The function of the intensifier/lens unit 90 is to intensify the ER beam 12 and focus it upon the multi-linear array 32. The multi-linear array 32 typically includes columns 42a, 42b, ... 42m and rows 44a, 44b, 44c ... of image sensing elements 40 as discussed in connection with FIG. 2. The multi-linear array 32 includes a horizontal shift register 48 at one end thereof into which signals from the respective columns 42a, 42b, ... 42n may be loaded. These signals, in turn, may be serially outputted over the signal bus 60 to a video system 92. Typically, the video system 92 will include an image data processor 94. This processor 94 interfaces with the multilinear array 32 and converts the signals received over the signal bus 60 into a suitable form for processing so that an appropriate image may be created from the signals and displayed. An image storage unit 96 may be coupled to the image data processor 94 in order to allow the image data processed by the image data processor 94 to be sampled, held and retrieved at appropriate time intervals. Also coupled to the image data processor 94 is an image display unit 98. This image display unit 98 could be realized using a conventional CRT tube (in which case the image data processor 94 would also include the appropriate circuitry to control and energize the CRT tube) or it could be a matrix display having a large number of small pixels that could be individually energized in accordance with respective control signals. Also included in the video system 92 would be a clock source 100. The clock source 100 would generate the appropriate vertical shift clocking signal 50 that is directed to the columns within the array 32 over signal bus 52, as well as the horizontal shift clocking signal 54 that is directed to the horizontal shift register 48 of the array 32 over the signal bus 56. As shown in FIG. 4, the vertical shift clocking signal 50 could also be used as an internal timing signal for the image data processor 94 and the image storage unit 96. Alternatively, or conjunctively, other appropriate internal and external timing signals could be generated by the clock source 50.

A significant feature of the invention herein disclosed is the control of the specimen table 26 by a table control unit 102. The relative motion of the table 26 with respect to the ER beam 12 must be synchronized with the clocking signals used in connection with the vertical and horizontal shaft registers of the multi-linear array 32. For example, the control unit 102 may move the specimen table 26 in the direction indicated by the arrow 104 through the ER beam 12 at a speed that is synchronized with the vertical shift clocking signal 50 used in connection with the columns of sensors 42a, 42b, ... 42m. This synchronization feature is of vital importance to the invention as discussed below in connection with the operation of the system.

The operation of the scanning radiographic system depicted in the block diagram of FIG. 4 will now be explained. A patient, or other opaque specimen, is placed on the specimen table 26. The specimen table 26 is then manually (or otherwise) moved to a desirable starting position. Once the specimen table has been moved to the initial starting position, the ER source 10 is energized. This energization may be continuous or pulsed. If pulsed, a clock signal synchronized with the vertical shift clocking signal 50 as received over the signal line 106 (shown in dotted lines) would be used to energize the ER source 10 at the appropriate pulsed intervals.

The ER beam 12 passes through the opaque specimen, the specimen table 26, and the intensifier/lens unit 90. The beam is appropriately focused on the multi-linear array 32 so that except for the effects of the opaque specimen, approximately the same intensity would be sensed at each small area on the surface of the array where the image sensing elements 40 (FIG. 2) are located. For convenience of explanation, each of these small areas (corresponding to each image sensing element 40) will be referred to as a photosite. Thus, in FIG. 4, the small square area at the intersection of column 42a with the row 44a would be a single photosite. In like fashion, the intersection of each column with each row, as depicted in FIG. 4, also comprises a single photosite.

In connection with the term "photosite" above described, the term "pixel" will also prove useful in the description that follows. At any instant of time, the radiation falling upon any single photosite of the array 32 is passing through a corresponding pixel of the opaque specimen 28. Thus, a "pixel" may be thought of as a small area of the opaque specimen through which the radiation falling upon a single photosite passes. Alternatively, a "pixel" may be thought of as a small cross-sectional area of the ultimately-produced radiograph image.

In operation, the radiation 12 passing through a horizontal line of pixels of the opaque specimen 28 is directed through the intensifier/lens unit 90 to fall upon a line of photosites located on the multi-linear array 32. In the context of this discussion, a "horizontal" line referrs to a line that is perpendicular to the direction of the relative motion of the specimen table, which direction of motion is indicated by the arrow 104. The signal sensed at each photosite (or at each image sensing element 40 (FIG. 2)) is vertically shifted from a first line (row) of the array to an adjacent line in response to the vertical shift clocking signal 50. At this same time, the specimen table is also shifted forward (in the direction of the arrow 104) so that the radiation now falling upon the second line of photosites is passing through the same line of pixels of the opaque specimen that previously fell upon the first line of photosites on the array 32. As this process continues, the signals being shifted vertically along the columns 42a, 42b, ... 42m of the array 32 each represent the accumulated signals corresponding to a single pixel of the opaque specimen 28. Thus, the individual pixels in the image that is ultimately produced result from an integration process, the integration occurring over the full length of the columns of the array 32. After this integration has occurred, the accumulated signals are passed into the horizontal shift register 48 and shifted serially therefrom in response to the horizontal shift clocking signal 54. Note that each pixel in the accumulated image is the result of $n\Delta t$ seconds of integration, where n is the number of lines or rows in the array 32, and $\Delta t = 1/f$, where f is the clocking frequency of the vertical shift clocking signal 50.

Where a charge coupled device (CCD) multi-linear array 32, such as is depicted in FIG. 3, is used with the invention, it is seen that the signals associated with the sensed radiation are charged packets of electrons (or holes) which are passed along the column shift registers. After the charge packet which resulted from charge accumulated at a first line of the CCD array 32 has passed to an adjacent line, the charge which accumulates at this adjacent line is added to that already in the shift register. In this way charges accumulate at each successive line until they passes into the horizontal shift register. Thus, as explained above, when an image is scanned along the CCD array 32 at the same rate that charge is passed from line to line, a non-blurred image results.

The above process results improved scan speed because the exposure of each individual photosite does not need to be near as long as prior art systems in that the total exposure may result from the accumulated exposure after the signal has been shifted through several photosites. Moreover, the resolution will also be improved. For example, if the ER beam 12 were to fall upon an area that were 15 cm by 2 cm at the surface of the opaque specimen 28, and if the resulting radiation passing therethrough were to be imaged onto a 380×244 array of a typical CCD device, a resolution of 0.4 mm×0.4 mm could be achieved. Moreover, by using an effective exposure time of 100 milliseconds per pixel, a scan speed of 20 cm/second could be realized. It should be noted that the image intensifier 20 (FIG. 1), which is included in the intensifier/lens unit 90 of FIG. 4, could be either a proximity type image intensifier or a flat florescent screen with efficient optical coupling.

While the above description has described a system wherein the signals or charges are shifted vertically along columns of the multi-linear array 32 so as to be synchronized with corresponding motion of the specimen table 26, it should be apparent that the motion of the specimen table and the opaque object could follow any known pattern so long as the shifting of the signals or charges from photosite to photosite of the multi-linear array 32 also followed the same pattern. Thus, a system could be envisioned wherein the accumulated signals received by the image data processor 94 could be analyzed to see if sufficient data were present to produce a desirable image. If not, suitable controls could be included within the video system 92 to cause the specimen table to back up (in order to get another run of data) or to move sideways, or diagonally, in order to get a more complete data package to represent the image of a particular portion of the opaque specimen. All that is required, is that such movement of the specimen table be synchronized with the shifting of the signals so that the augmentation of the signals at each photosite corresponds to radiation that has passed to the same pixel area of the opaque specimen.

The source of electronic radiation 10 will typically be an X-ray source, although any other suitable radiation could be used, such as gamarays. The type of radiation used will depend in large extent to the type of opaque specimens that are to be analyzed.

The table control unit 102 could be realized with a stepper motor (as when the ER beams 12 are pulsed rather than continuous), or it could simply be a motor of any suitable type controlled through known serve control techniques to syncrhonize the specimen table's motion with the shifting of the signals within the array 32. It would also be possible, of course, to keep the specimen table stationary and move in unison the source of ER 10, the intensifier/lens unit 90, and the array 32, thereby creating the requisite relative motion between the ER beam 12 and opaque specimen 28.

While the invention herein disclosed has been described by means of specific embodiments and applications thereof, numerous modifications and variations could be made thereto by those skilled in radiography and electronic art without departing from the spirit and scope of the present invention. It is therefore to be understood that within the scope of the appended claims, the invention may be practiced otherwise than as specifically described herein.

What is claimed is:

1. A radiographic system for generating a radiograph-type image of an opaque specimen comprising:
   means for generating a beam of radiation;
   an array of sensors aligned with said beam comprising:
      a plurality of sensors, each adapted to sense and signal the intensity of any radiation falling thereon, signal connection means for connecting said sensors of said array in columns, said signal connection means being adapted to allow signals from each of said sensors of a given column to be shifted to an adjacent sensor of said given column in response to a shift control signal, and data output means for outputting signals from said columns in response to an output control signal;

image display means responsive to said outputted signals from said data output means for producing an image representative of said outputted signals;

motion means for transversing said beam of radiation with said opaque specimen in a direction that is substantially parallel with said columns of said sensors; and synchronization means for generating said shift control and output control signals and synchronizing them with the relative motion between said opaque specimen and said beam of radiation, whereby said opaque specimen passes through said beam of radiation at substantially the same rate as said signals of said sensors are shifted along said columns of sensors of said planar array.

2. A radiographic system as defined in claim 1 wherein said data output means comprises a shift register having a plurality of elements adapted to shift a signal from one element of said register to an adjacent element of said register in response to said output control signal, an end element of said register having an output port through which said signals may be serially outputted to said image display means, and each element of said register having an input port coupled to an end sensor of a respective column of said sensors, whereby said signals being shifted through said columns in response to said shift control signal may be loaded in parallel into said shift register.

3. A radiographic system as defined in claim 2 wherein said output control signal operates at a substantially faster rate than said shift control signal, whereby said shift register, in response to said output control signal, may be completely emptied in serial fashion before being reloaded in parallel in response to said shift control signal.

4. A radiographic system as defined in claim 3 wherein the frequency of said output control signal is at least $n \times f$, where f is the frequency of said shift control signal and n is the number of elements in said shift register.

5. A radiographic system as defined in claim 3 wherein said motion means comprises:
a holding surface onto which said opaque specimen may be placed, said holding surface being adapted to allow said radiation to pass therethrough;
drive means for moving said holding surface through said beam.

6. A radiographic system as defined in claim 5 further including lens means for focusing said beam of radiation onto said array after said beam has passed through said holding surface and opaque specimen.

7. A radiographic system as defined in claim 6 further including image intensifier means for collecting and intensifying said beam of radiation after said beam has passed through said holding surface.

8. A radiographic system as defined in claim 5 wherein said image display means comprises:
an image data processor for buffering and processing the outputted signals received from said data output means;
image storage means coupled to said image data processor for storing said buffered and processed signals; and
an image display coupled to said image data processor for receiving said buffered and processed signals and converting them to an image representative of said buffered and processed signals.

9. A radiographic system as defined in claim 8 wherein said image display comprises a cathode-ray tube.

10. A radiographic system as defined in claim 5 wherein said array comprises a two dimensional charge coupled device, wherein each of said sensors comprises a photodetector, each of said photodetectors being adapted to generate an electrical charge proportional to the intensity of the radiation falling thereon, said two dimensional charge coupled device including:
a first group of charge transfer gates connecting different groups of said photodetectors in series in a first dimension so as to form a plurality of photodetector columns, said first group of charge transfer gates comprising said signal connection means and being adapted to allow the electrical charges generated by said photodetectors to be serially shifted through said photodetector columns in response to said shift control signal; and
a second group of charge transfer gates connecting an upper end of said photodetector columns in a second dimension so as to form a charge transport row, said charge transfer row comprising said data output means and being adapted to allow electrical charges from said photodetector columns to enter thereinto in parallel and be serially shifted thereacross in response to said output control signal.

11. A radiographic system as defined in claim 10 wherein said data output means further includes an output gate connected in series with said charge transport row, said output gate being responsive to said output control signal and being adapted to interface said charge transport row with said image display means, whereby the electrical charges being shifted across said charge transport row may be serially passed through to said image display means.

12. A method for producing a radiograph-type image of an opaque specimen having increased resolution and imaging speed, comprising the steps of:
(a) constructing a multi-linear array having a plurality of radiation sensors arranged in columns and rows thereon, each of said sensors being adapted to generate an intensity signal proportional to the intensity of the radiation sensed thereby, and each of said sensors having a storage element connected thereto;
(b) aligning a beam of radiation with said multi-linear array;
(c) storing said intensity signals of each sensor in its respective storage element;
(d) shifting the intensity signals stored in each of said storage elements to a different storage element at controlled time intervals, said adjacent storage element being connected to a radiation sensor that is adjacent to the radiation sensor having the storage element from where the intensity signals are shifted;
(e) augmenting the intensity signals of said storage elements after the shifting of step (d) in order to account for newly generated intensity signals received from the respective radiation sensors connected to each of said storage elements;

(f) creating relative motion between said opaque object and said array, said opaque object moving with respect to said array at a controlled speed;

(g) synchronizing the shifting of step (d) with the relative motion of step (f) so that the augmenting of step (e) is always based on intensity signals derived from sensed radiation passing through substantially the same small cross-sectional areas of said opaque object.

(h) repeating step (d), (e), (f), and (g) until the opaque object has passed completely through said beam of radiation, (i) processing the augmented signals to create a radiograph-type image, each of said augmented signals representing the accumulated radiation that has passed through a specific small cross-sectional area of said opaque object during the time said opaque object was moving through said beam of radiation.

13. A method for producing a radiograph-type image as defined in claim 12 wherein step (a) of constructing a multi-linear array comprises constructing said array from a two dimensional charge coupled device.

14. A method as defined in claim 12 wherein step (f) of creating relative motion between said opaque object and said array comprises fixing said array and said beam of radiation and passing said opaque object therebetween.

15. A method as defined in claim 12 wherein step (f) of creating relative motion between said opaque object and said array comprises fixing said opaque object and moving said array therebelow and said beam of radiation thereabove.

16. A scanning radiographic system comprising:
a multi-linear array having a plurality of radiation sensors lying in a single plane and arranged in an ordered fashion, each of said sensors being adapted to generate an intensity signal proportional to the intensity of the radiation sensed thereby, said multi-linear array including:
holding means for holding the intensity signals generated by each of said radiation sensors, each of said holding means being adapted to up-date the intensity signal held therein with other newly generated intensity signals resulting from additional radiation sensed by its respective sensor,
first shifting means for serially shifting said updated signals through the holding means associated with defined groups of said sensors in response to a first clock signal, said defined groups of sensors comprising specified patterns of said radiation sensors, and second shifting means for serially shifting said updated signals out of the holding means associated with at least one of the sensors of each of said defined groups of sensors in response to a second clock signal;

a clock source for generating said first and second clock signals;

placement means for placing an opaque specimen to be scanned by said radiographic system above said multi-linear array;

motion means for creating relative motion between said placement means and multi-linear array, said motion means being adapted to cause the relative motion thus created to follow a course substantially the same as said specified patterns;

a source of radiation placed above said placement means for directing a beam of radiation through said opaque specimen and onto said array; and synchronization means for synchronizing said motion means with said first clock signal, whereby the speed and course of travel of a particular updated signal through the holding means of a given group of said sensors is optically aligned with the speed and course of travel of the radiation passing through the given area of said opaque specimen.

17. A scanning radiographic system as defined in claim 16 further including data processing means adapted to receive said up-dated signals from said second shifting means in response to said second clock signal.

18. A scanning radiographic system as defined in claim 17 wherein said data processing means includes
an image data processor to receive, process, and manipulate said up-dated signals; and
an image display responsive to said processed and manipulated up-dated signals for displaying an image that is derived from said signals.

19. A scanning radiographic system as defined in claim 18 wherein said multi-linear array comprises a charge coupled device.

20. A scanning radiographic system as defined in claim 19 wherein said radiation sensors are arranged in tightly compacted columns and rows lying on the plane of said array.

21. A scanning radiographic system as defined in claim 20 wherein said first shifting means includes a plurality of vertical shift registers, each of said vertical shift registers being coupled to a respective column of said radiation sensors.

22. A scanning radiographic system as defined in claim 21 wherein said second shifting means comprises a horizontal shift register coupled to one end of said plurality of vertical shift registers.

* * * * *